United States Patent [19]
Reiss

[11] Patent Number: 5,324,317
[45] Date of Patent: Jun. 28, 1994

[54] INTERFERENTIAL STIMULATOR FOR APPLYING LOW FREQUENCY ALTERNATING CURRENT TO THE BODY

[75] Inventor: Hans W. Reiss, Encinitas, Calif.
[73] Assignee: Medserve Group, Inc., Vista, Calif.
[21] Appl. No.: 953,945
[22] Filed: Sep. 30, 1992
[51] Int. Cl.⁵ .............................................. A61N 1/36
[52] U.S. Cl. ........................................ 607/67; 607/66
[58] Field of Search ......................... 607/66, 67, 70, 72

[56] References Cited

U.S. PATENT DOCUMENTS

| | | | |
|---|---|---|---|
| 2,622,601 | 10/1948 | Nemec | 607/67 |
| 3,294,092 | 9/1965 | Landauer | 607/66 |
| 3,774,620 | 11/1973 | Hansjürgens | 607/67 |
| 3,794,022 | 2/1974 | Nawracaj et al. | 607/67 |

*Primary Examiner*—Lee S. Cohen
*Assistant Examiner*—Jeffrey R. Jastrzab
*Attorney, Agent, or Firm*—Frank D. Gilliam

[57] ABSTRACT

An interferential stimulator for applying two medium frequency alternating currents of slightly differing frequencies to the body of a living being so that they cross and interact to produce a low frequency therapeutic current at a selected point. A fixed frequency is generated and applied to the skin through a first electrode pair. A second frequency, differing from the first by from about 1 to 150Hz is applied through a second electrode pair. The electrodes are arranged to deliver a localized stimulation. At the crossing point of the four electrodes a low frequency beat or pulse is produced by the heterodyne process for specific point stimulation. The stimulator may be operated in any of several modes. First, constant stimulation may be applied at fixed frequency difference between electrodes. Second, the frequency difference can be decreased abruptly and returned to the original frequency difference over about 1 second. Third, the frequency difference can be decreased abruptly about 50% and returned over a typically 8 second period. Fourth, a gradual about 50% drop in frequency difference may be accomplished gradually and returned over typically a 10 second period. This device has been found to be useful in reducing pain, and appears to provide benefits in reducing edema and inflammation, increasing blood flow and reducing muscle spasms.

25 Claims, 3 Drawing Sheets

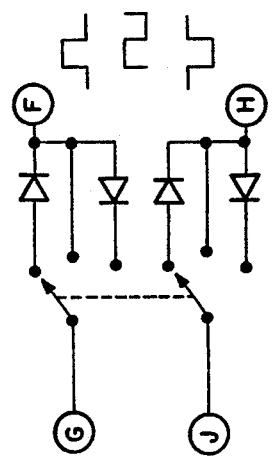
FIGURE 3c
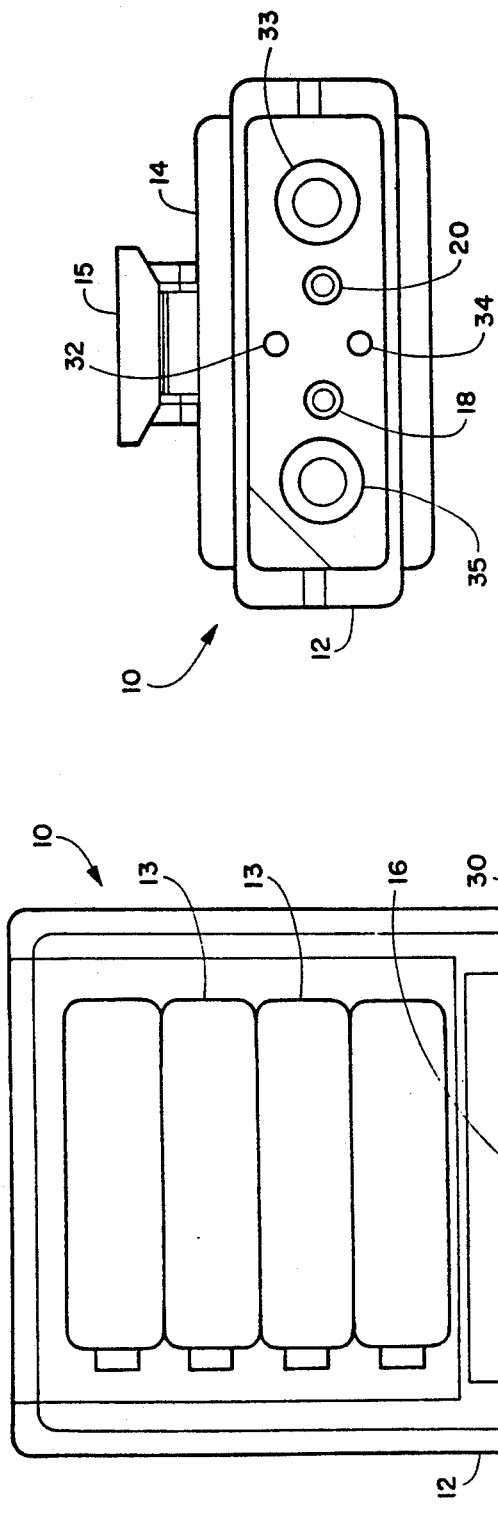
FIGURE 2
FIGURE 1

INTERFERENTIAL STIMULATOR FOR APPLYING LOW FREQUENCY ALTERNATING CURRENT TO THE BODY

BACKGROUND OF THE INVENTION

This invention relates in general to electrotherapy apparatus and, more specifically to an interferential generator for treating a living body with low frequency therapeutic current at a selected point.

A wide variety of transcutaneous electrical nerve stimulation (TENS) devices have been developed to deliver electrical current to an area of a living body, typically a human being, to alleviate pain. Typical of these is U.S. Pat. No. 4,989,605 to Rossen, which applies a carrier signal to the skin through an electrode. The signal is in the form of D.C. bursts in the frequency range of 10,000 to 19,000Hz which is modulated on and off at a lower frequency. Other typical TENS type devices include the microprocessor controlled device for applying a low frequency pulse train and a modulated high frequency pulse train to a patient through an electrode as disclosed by Padjen et al in U.S. Pat. No. 4,719,922, a device in which a constant current square wave signal is directed into the body between two electrodes as described by Hudleson et al in U.S. Pat. 4,232,680 and a device in which a high frequency low amperage current is applied to a body through an electrode as described by Liss et al in U.S. Pat. No. 3,902,502.

The prior art TENS devices deliver a wide area stimulation, rather than the generally preferable localized stimulation. Also, prior art devices tend to provide a uniform signal throughout a treatment. The body tends to accommodate to the stimulation, lessening its effectiveness over time. While of varying effectiveness, the prior devices are not as effective as would be desired in treating pain and other conditions. Thus, there is a continuing need for electrotherapy devices of improved effectiveness.

SUMMARY OF THE INVENTION

The interferential stimulation device of this invention delivers localized stimulation rather than broad area stimulation by the use of four contact points and two different frequencies that, at the crossing point, produce a low frequency beat by the heterodyne process for specific stimulation at the crossing point.

Fixed frequency generation means generates a fixed frequency of from about 1,000 to 20,000Hz. Best results have been obtained at about 4000Hz. An interference frequency generation means generates a selected frequency of from about to 1,000Hz different from the fixed frequency. Optimally, this frequency is from about 1 to 150Hz greater than the fixed frequency. This produces a beat frequency equal to the difference in the two generated frequencies, typically from about 1 to 150 beats per second. These pulses preferably are biphasic square wave pulses with a fixed pulse width of from about 10 to 50 microseconds, with about 125 microseconds preferred.

The interferential stimulator includes a mode control to permit changing the sequence of stimulation to prevent accommodation to the unit and to enable a number of alternatives to be evaluated to find the most effective pain relief. In the first mode, the unit is operated in a continuous manner at one set of frequencies. In a second mode the stimulator operates at a set pulse rate for a short period, such as about one second, drops to a much lower pulse rate, such as about 50% for a short period, such as about one second, then repeats. In a third mode, the stimulator operates at a set pulse rate for a period of from about 1 to 15 seconds (preferably about 8 seconds), drops to a much lower rate, typically about 50%, for from about 1 to 15 seconds (preferably the same length as the first period), then repeats. In a fourth mode, the stimulator operates at a set pulse rate for a period of from about 1 to 15 seconds (preferably about 10 seconds) then slowly drops to a much lower pulse rate, typically about 50% of the set value over a period of from about 1 to 15 seconds (preferably the same as the initial operation period), then repeats. These periods, degree of decrease between sequences and the initial set pulse rate may be varied, where suitable, if desired.

Any suitable output voltage and amperage may be used. Preferably, output voltage ranges from 0 to 25 volts (50 volts peak-to-peak) and the output current varies from about 0 to 50 milliamps. The treatment may be continued for any suitable period, with the different modes used for different portions of the treatment, as desired. In general, treatments of up to about 60 minutes are preferred, with the time period controlled by a variable timer included in the unit.

For best results, a bi-polar circuit with four electrodes are used, one applying the fixed frequency, one applying the interference frequency and two neutral electrodes. The electrodes are preferably arranged in a circular, square or other closed figure pattern with the application electrodes and neutral electrodes alternating around the figure. This provides optimum localization of the stimulation at the center of the figure. If desired, the frequency mixing may be done internally, with the mixed signal being applied through one electrode spaced from a neutral electrode.

BRIEF DESCRIPTION OF THE DRAWING

Details of the invention, and of certain preferred embodiments thereof, will be further understood upon reference to the drawing, wherein:

FIG. 1 is a plan view of the interferential stimulator of this invention with the cover removed;

FIG. 2 is a front elevation view of the interferential stimulator of this invention with cover in place; and FIG. 3a, 3b and 3c when combined make up the schematic circuit diagram of the operating system of the stimulator.

DETAILED DESCRIPTION OF PREFERRED EMBODIMENTS

Figure 3A:
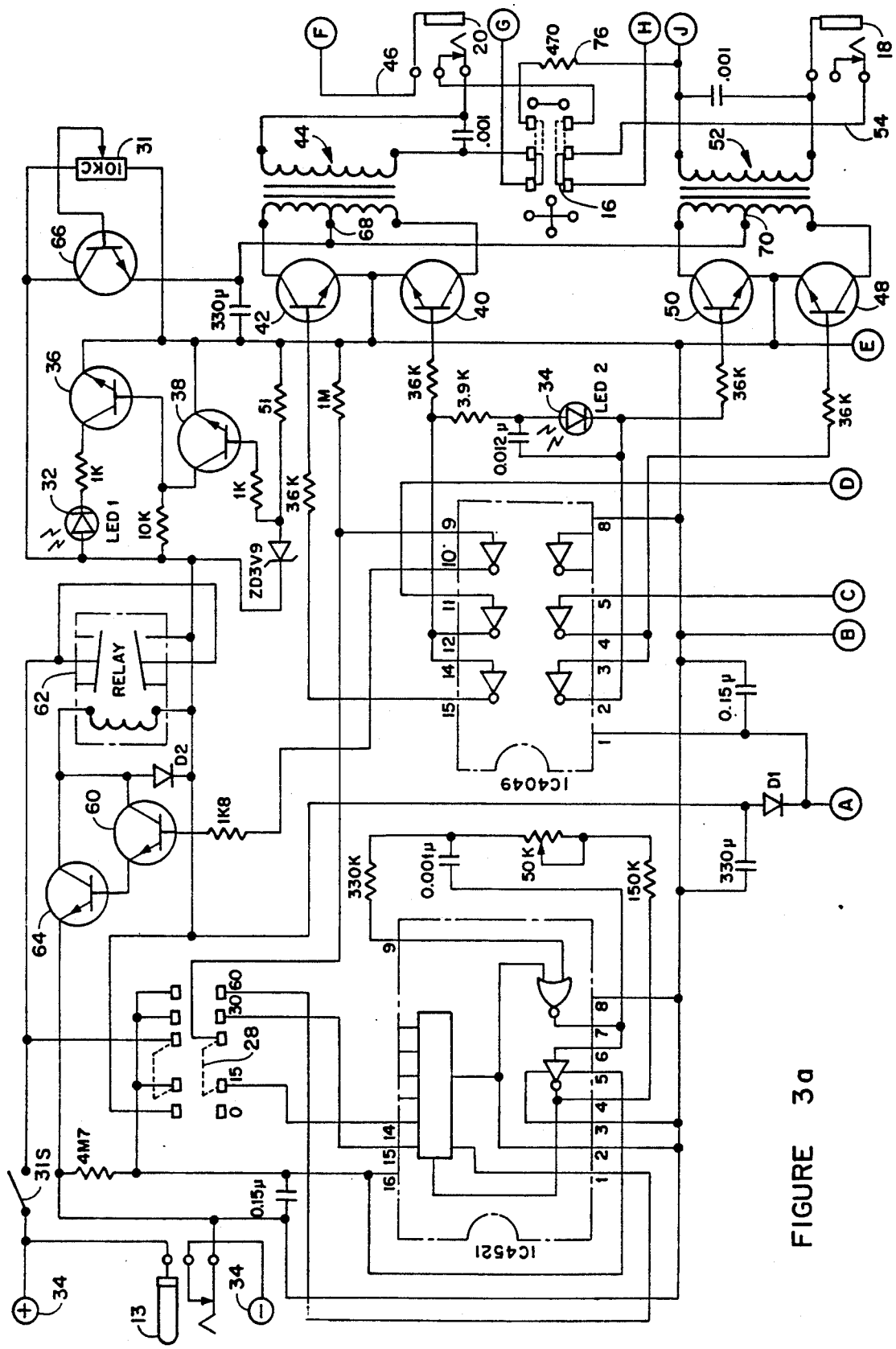

Referring now to FIG. 1, there is seen an interferential stimulator 10 including a housing 12 containing the batteries 13 and electrical components and carrying electrode jacks and operating switches. The rear portion of top 14 of housing 12 is slidable to the rear to reveal the battery compartment, which typically contains four AA batteries, as seen in FIG. 1, shown with the cover removed. As seen in FIG. 2, a conventional plastic clip 15 may be secured to bottom of 14 so that the unit can be clipped to the user's belt or the like.

A conventional DC jack (not shown) may be provided, typically at the back of the unit, below the batteries, for use as a battery eliminator in a conventional manner. A conventional rotary type on/off switch which is part of the amplitude control 31 is provide for activating the stimulator.

A pair of jacks 18 and 20 are provided on the front panel for connection to the fixed frequency electrode 22 and the interference frequency electrode 24, respectively, and their associated neutral electrodes 23 and 25. An electrode switch 16 on the front panel allows selection of the four electrode position where interferential frequencies are mixed at the crossing point of the electrodes or the two electrode position where the frequency mixing is done internally and only one jack 18 is used.

A slide timer switch 28 is provided on the front panel. This switch can be set to "0" to allow the unit to run continuously, or to any selected period, typically up to 60 minutes with selected intermediate settings. A slide mode switch 30 is provided to permit selecting which of the four operational modes is to be used, as detailed above. A rotary control 35 is used to select the low frequency pulse rate, typically from about 1 to 150.

A first light emitting diode 32 is provided on the top panel 14 to indicate low battery conditions. A second light emitting diode 34 is a frequency indicator, connected to flash at the rate of the low frequency beat.

Figure 3B:
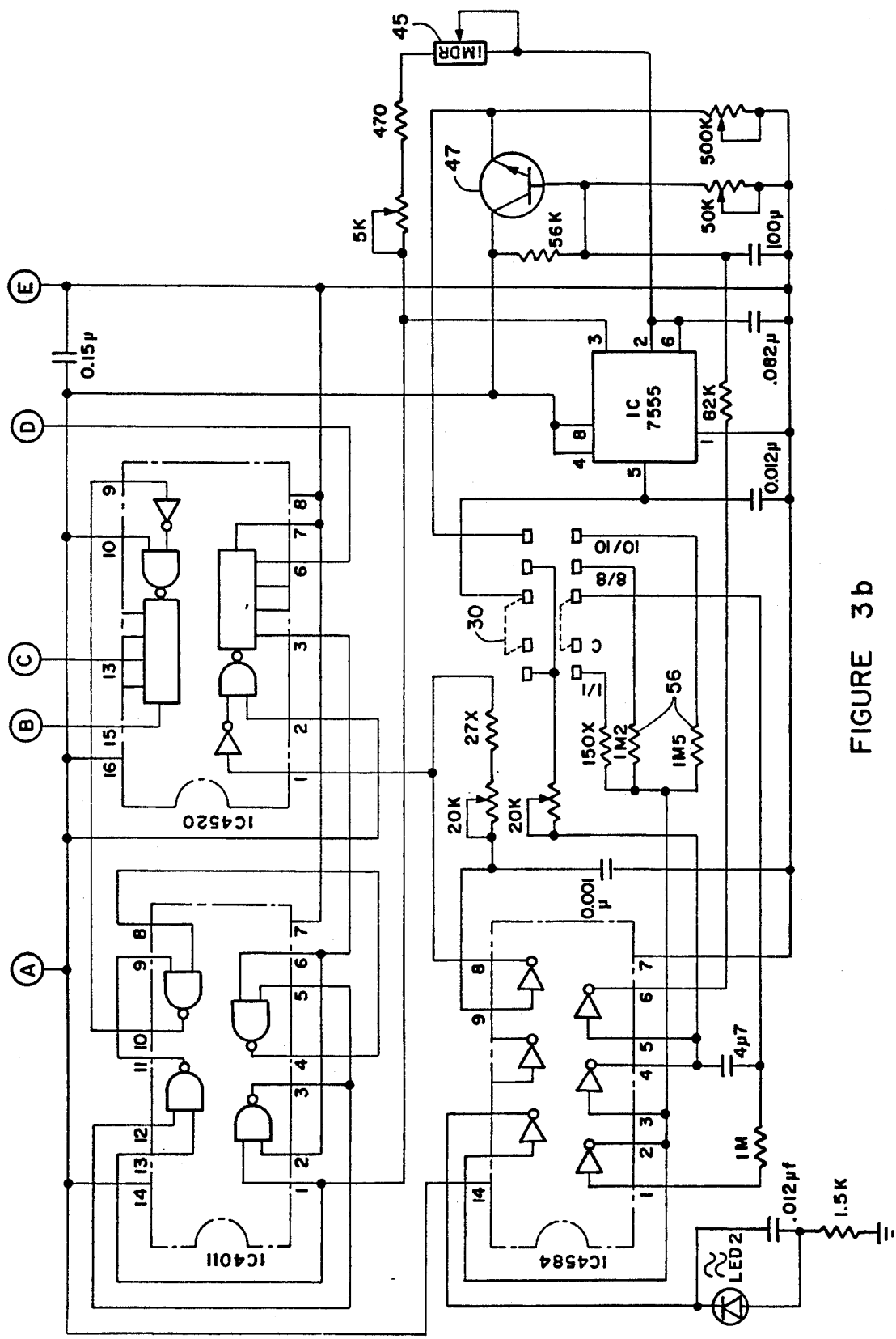

FIG. 3 provides a schematic circuit diagram for the interferential stimulator circuit. The circuit receives 6v DC power from batteries through contacts 34. The unit is turned on by the switch which is part of amplitude control 31. Low battery conditions are indicated when light emitting diode 32 begins to glow, under the control of transistors 36 and 38.

The circuit supplying the fixed frequency begins with IC4584, which is a hex schmitt trigger used as the primary oscillator (typically available from Motorala Semiconductor). The output at pin 8 is a 64,000Hz square wave, which is connected to the clock input of IC4520 (typically available from Motorala Semiconductor) a binary counter at pin 1. The divide-by-16 output (4000Hz) of IC4520 is connected to IC4049 (typically available from Motorala Semiconductor), a hex invertor, at pin 11. The output pin 12 of IC4049 is connected to drive transistor 40 and to pin 14 of IC4049. The inverted output at 15 is connected to the other drive transistor 42. This pair of transistors 40 and 42 drive first transformer 44 for a fixed output on first channel 46 of 4000Hz.

The interference frequency generation means provides a variable 4001 to 4150Hz output. From pin 3 (the divide-by-two output) of IC4520 a 32,000 square wave is connected to IC4011 (typically, available from Motorala Semiconductor) at pins 6 and 2, where it is mixed with the output of IC7555 (typically available from Harris Semiconductor) from pin 3. IC7555 is an 8 to 1200Hz oscillator. The frequency to be used is selected by variable resistor 31 which is adjusted by the front panel frequency control 33 (FIG. 2). The 32008 to 33,200Hz output of this mixing at pin 10 of IC4011 is connected to the clock input of the second half of IC4521 at pin 9, the divide by 8 output (4001 to 4150 Htz.). Pin 13 is connected to the Hex inverter Pin 5, Pin 4 is connected to pin 3 and to drive transistor 48. The inverted output at Pin 2 of IC4049 is connected to the other drive transistor 50. This pair of transistors 48 and 50 drive second transformer 52 for the 4001 to 4150Hz output to second channel 54.

Mode switch 30 (FIG. 1) selects the different modes described above by selecting different resistors 56 which in combination with a capacitor and the output from the primary oscillator, IC4584, form a control loop that modulates the control voltage pin 5 of IC7555, which changes the output frequency of the variable frequency oscillator the amount required to meet the selected position.

The time period of operation is controlled by IC4521 (typically available from Motorala Semiconductor), a 24-stage frequency divider with a built in RC oscillator. Output pins 1, 14 and 15 are selected by the timer selection switch 28 for periods of 15, 30 and 60 minutes of operation. For example, output pin 14 of IC4521 is a divide-by-4,194,304. This divided by 15 minutes is 279,620, which when divided by 60 seconds gives the oscillator frequency of 4660Hz. Of course, other time periods could be selected. When the selected time has expired the output pin goes low and places a low signal on pin 9 of IC4049 which gives a high out Pin 10 to the base of transistor 60, turning it off which releases relay 62, turning off power to the system until it is reset. The circuit transistors are the type 2SC2120 or equivalent thereto.

Amplitude is controlled by a 10,000 ohm variable resistor 31 that controls the base voltage to transistor 66, connected from the +6 volt contact 34 to the center taps 68 and 70 of transformers 44 and 52, respectively. The outer connections of transformers 44 and 52 are connected to the collectors of transistors 40, 42 and 48, 50, respectively. Controlling this voltage varies the amplification of transistors 40, 42, 48 and 50 and, therefore, the output.

Electrode switch 16 controls the connections to the output jacks 18 and 20 for the two channels. In the four wire position jacks 18 and 20 are isolated from each other and normal interferential stimulation occurs. In the two wire position, the outputs are mixed across 470 ohm resistor 76 and output 18 has the mixed signal, a 1 to 150Hz beat.

Thus it is apparent that this is a precise and variable system for selectively providing a variety of therapeutic interferential signals to a patient.

Other applications, variations and ramifications of this invention will occur to those skilled in the art upon reading this disclosure. Those are intended to be included within the scope of this invention, as defined in the appended claims.

I claim:
1. An interferential stimulator which comprises:
   fixed frequency signal generation means for generating a fixed frequency signal of from about 1,000 to 20,000Hz;
   at least one first electrode means for receiving said fixed frequency signal and imposing said fixed frequency signal on the skin of a living body;
   interference frequency signal generation means for generating a selected interference frequency signal from about 1 to 1000Hz different from said fixed frequency signal;
   at least one second electrode means for receiving said interference frequency signal and imposing said interference frequency signal on the skin of a living body at a location spaced a selected distance from said at least one first electrode means to generate a selected interference pulse rate at a location below the skin; and
   mode control means for controlling an operating mode of the stimulator including means for selectively providing any one of the following operating modes:
   (a) continuing application at the selected interference pulse rate;

(b) rapidly varying the selected interference pulse rate between an initial selected interference pulse rate and a second, different, interference pulse rate;

(c) operating at an initial selected interference pulse rate for from about 1 to 15 seconds, then rapidly changing the interference pulse rate to a second, different, interference pulse rate for from about 1 to 15 seconds, then repeating this sequence for a selected period; and (d) operating at an initial selected interference pulse rate for from about 1 to 15 seconds, then changing the interference pulse rate gradually over from about 1 to 15 seconds to a second, different, interference pulse rate, maintaining the second interference pulse rate for about 1 to 15 seconds, then repeating this sequence for a selected period.

2. The interferential stimulator according to claim 1 wherein said fixed frequency signal is 4000Hz and said interference frequency signal is from about 1 to 150Hz greater than said fixed frequency signal.

3. The interferential stimulator according to claim 1 further including timer means for turning the stimulator off after a selected time period.

4. The intereferential stimulator according to claim 1 further including means for selectively varying amplitudes of the fixed and interference frequency signals.

5. The interferential stimulator according to claim 1 wherein the stimulator is capable of being powered by batteries and further including a first light emitting diode, means for sensing when battery power is low and means for turning on the first light emitting diode when a low battery power condition is sensed.

6. The interferential stimulator according to claim 5 further including a second light emitting diode, means for sensing the interference pulse rate and means for causing the second light emitting diode to flash in accordance interference with the pulse rate.

7. The interferential stimulator according to claim 1 further including means for adjusting an output current of said fixed frequency and interference frequency signals to a value no greater than about 50 milliamps and adjusting an output voltage of said fixed frequency and intereference frequency signals to a value no greater than about 25 volts.

8. The interferential stimulator according to claim 1 wherein said fixed frequency and interference frequency signals have symmetrical biphasic square waveforms and form interference pulses having pulse widths of about 125 microseconds for each phase.

9. The interferential stimulator according to claim 8 wherein said interference pulses have a positive polarity.

10. The interferential stimulator according to claim 8 wherein said interference pulses have a negative polarity.

11. The interferential stimulator according to claim 1 including means for mixing said fixed frequency and interference frequency signals within the stimulator, said mixing resulting in pulses and a single electrode means for application of the resulting pulses to the skin.

12. The interferential stimulator according to claim 1 wherein the means for providing the operating mode of paragraph (b) includes means for decreasing the pulse rate to a lower pulse rate of about 50% of the initial pulse rate after about 1 second, to continue the lower pulse rate for about 1 second and to repeat that sequence for a selected period.

13. The interferential stimulator according to claim 1 wherein the means for providing the operating mode of paragraph (c) includes means for continuing the initial pulse rate for about 8 seconds, for rapidly decreasing the pulse rate to a lower pulse rate of about 50% of the initial pulse rate, for maintaining the lower pulse rate for about 8 seconds and to repeat that sequence for a selected period.

14. The interferential stimulator according to claim 1 wherein the means for providing the operating mode of paragraph (d) includes means for continuing the initial pulse rate for about 10 seconds, for gradually changing to the second pulse rate over about 10 seconds, for holding the second pulse rate for about 10 seconds, and to repeat that sequence for a selected period.

15. The interferential stimulator according to claim 1 wherein the means for providing the operating mode of paragraph (d) includes means for setting said pulse rate at an initial value, for gradually changing the initial pulse rate to a second pulse rate over about 10 seconds and to repeat that sequence for a selected period.

16. A method of providing interferential stimulation to the skin of a living body which comprises the steps of:

producing a first electrical signal at a first fixed frequency of from about 1,000 to 20,000Hz;

producing a second electrical signal at an interference frequency of from about 1 to 150Hz different from said fixed frequency;

applying the first and second signals to the skin of a living body at selected application locations so that a low frequency pulse at a pulse frequency equal to the difference in frequency between said fixed frequency and said interference frequency is applied to said body at a selected pulse rate; and selecting and applying one of the following treatment operation modes:

(a) continuing application at an initial selected pulse rate;

(b) rapidly varying pulse rate between said initial selected pulse rate and a second, different, pulse rate;

(c) operating at said initial selected pulse rate for from about 1 to 15 seconds, then rapidly changing pulse rate to a second, different, pulse rate for from about 1 to 15 seconds, then repeating this sequence for a selected period; and (d) operating at said initial selected pulse rate for from about 1 to 15 seconds, then changing the initial selected pulse rate gradually over from about 1 to 15 seconds to a second, different, pulse rate, maintaining the second pulse rate for no longer than about 15 seconds, then repeating this sequence for a selected period.

17. The method according to claim 16 wherein said fixed frequency is 4000Hz and said interference frequency is from 4001 to 4150Hz to produce a pulse rate of from 1 to 150 pulses per second.

18. The method according to claim 16 wherein the pulse rate of paragraph (b) is decreased to about 50% of the initial pulse rate after about 1 second, the resulting lower pulse rate is continued for about 1 second, the pulse rate is returned to the initial pulse rate and the changes in pulse rate are repeated for a selected period.

19. The method according to claim 16 wherein the initial pulse rate of paragraph (c) is continued for about 8 seconds, the pulse rate is rapidly decreased to about 50% of the initial pulse rate for about 8 seconds, the pulse rate is returned to the initial pulse rate and the changes in pulse rate are repeated for a selected period.

20. The method according to claim 16 wherein the pulse rate of paragraph (d) is maintained at the initial pulse rate for about 10 seconds, gradually changed to the second pulse rate over about 10 seconds, holding the second pulse rate for about 10 seconds, then returning the pulse rate to the initial value and then repeating, the changes in pulse rate for a selected period.

21. The method according to claim 16 wherein the pulse rate of paragraph (d) is set at an initial value, the pulse rate is gradually changed to a second pulse rate over about 10 seconds and upon reaching the second pulse returning the pulse rate to the initial value and repeating the changes in pulse rate for a selected period.

22. The method according to claim 16 further including the steps of adjusting an output current of said signals to a value no greater than about 50 milliamps and adjusting an output voltage of said signals to a value no greater than about 25 volts.

23. The interferential stimulator according to claim 1 wherein said fixed frequency and interference frequency signals have symmetrical biphasic square waveforms and pulse widths of about 125 microseconds for each phase.

24. The method according to claim 16 wherein said first and second signals are applied to the skin through separate electrodes whereby the signals are mixed and the low frequency pulses are formed within the body.

25. The method according to claim 16 wherein said first and second signals are applied to the body through a single electrode.

* * * * *